United States Patent
Ricketts

(10) Patent No.: US 6,348,206 B1
(45) Date of Patent: Feb. 19, 2002

(54) COMPOSITION AND METHOD FOR PRODUCING LUBRICATING, GERMICIDE FOAM

(75) Inventor: David J. Ricketts, Irvine, CA (US)

(73) Assignee: Devtech Marketting, Inc., Irvine, CA (US)

( * ) Notice: Subject to any disclaimer, the term of this patent is extended or adjusted under 35 U.S.C. 154(b) by 0 days.

(21) Appl. No.: 09/585,512

(22) Filed: Jun. 1, 2000

Related U.S. Application Data

(63) Continuation-in-part of application No. 09/406,039, filed on Sep. 27, 1999, now abandoned.

(51) Int. Cl.$^7$ .............................................. A01N 25/16
(52) U.S. Cl. ........................................ 424/405; 424/45
(58) Field of Search ......................... 424/47, 405, 438, 424/672; 114/14.47, 651, 652, 673; 514/571, 738

(56) References Cited

U.S. PATENT DOCUMENTS

| | | | |
|---|---|---|---|
| 3,713,423 A | * | 1/1973 | Sparr, Sr. ...................... 119/1 |
| 5,720,984 A | * | 2/1998 | Ricketts ...................... 424/672 |

\* cited by examiner

*Primary Examiner*—Jose' G. Dees
*Assistant Examiner*—Konata M. George
(74) *Attorney, Agent, or Firm*—Willie Krawitz

(57) ABSTRACT

A skin cleaning, bacterial control, foam solution is provided, which enables a user to wash without requiring pre-wetting with water; this is followed by rinsing off the foam. The foam solution product is produced by mixing foaming and cleaning ingredients, active bacterial control ingredients, and water with a gas such as air, $CO_2$, nitrogen, propellant, etc., to make the foam. The foam solution and method enables a improved coverage, better penetration, less time, and the least amount of active ingredients for controlling microorganisms when used for personal care washing. The lubricity of the water enables an easier wash, without the prior application of water; the wash is then followed by rinsing. The method for producing a foam surfactant suitable for a combined bovine teat dip and teat wash comprises air pressurization of a surfactant solution containing a germicide, disinfectant, biocide, etc., passing the air-surfactant mixture through a flow or line mixer to a foam holding cup adjacent the teat area and expanding the mixture to atmospheric in the holding cup to produce an adherent surfactant foam product with reduced run-off, which both protects and reduces infection of the teat, particularly at the teat canal and surrounding udder area.

8 Claims, No Drawings

COMPOSITION AND METHOD FOR PRODUCING LUBRICATING, GERMICIDE FOAM

This application is a continuation-in-part of Ser. No.: 09/406,039 filed on Sep. 27, 1999, and now abandoned.

BACKGROUND OF THE INVENTION

This invention relates to a new and improved foam for hand wash and skin care which may be used for surgical scrubs, other sanitizing purposes, and for animal care such as bovine teat dips and teat washes, and the like.

Foam detergents and foam soaps have long been known, and in the case of hospital use, these soap and detergent foams are commonly used in conjunction with pre-wetting, followed by washing with the foam, and then rinsing off. This prior art procedure has the advantage of foaming less material, but has the disadvantage of uneven mixing with water from a pre-wetting, and hence, requires higher levels of active ingredients to effect reduction of microorganisms. Storage of ready-to-use foaming liquids can be reduced by providing concentrates which are diluted with water prior to use. However, the foam produced would not be suitable where a user has significantly contaminated hands and hence would prefer to avoid using a wet (or dry) cleaning paper which would require disposal, and hence form a contaminated storage area.

Innumerable germicide detergents, soaps and surfactants have been described in the past, but they cannot be used as a washable foam since they all require a pre-wetting prior to use since they lack the necessary inherent lubricity. Many of the same soaps, detergents, and surfactants produce foam when a foaming agent is added, however, such a foaming capability only becomes apparent when used with a foaming agent and combined with water. For example, in Applicant's U.S. Pat. No. 5,720,984 there is described a surfactant useful for hand care, which contains a foam-thickener and which becomes activated when combined with water. However, there is no disclosure concerning the formation of foam mixtures, and this is also typical for the surfactants listed in the annual publications by McCutcheon's, infra, and incorporated by reference herein.

Also, a large number of lubricants are known for use in cosmetics, pharmaceuticals and food, and these lubricants are listed in "McCutcheon's Functional Materials", Volume 2, North American Edition, 1994, (and succeeding yearly editions, through 1999 and incorporated by reference, herein) which is published by The Manufacturing Confectioner Publishing Co. However, none of these lubricants have been used in conjunction with a foam having inherent lubricating properties, and which may be used without a pre-wetting step.

An object of this invention is to provide a method for production and a germicide foam product therefrom which may be used as a foam wash for personal care and for cleaning equipment due to the internal lubricity of the foam, which does not require pre-wetting with water, and following a foam wash, the foam is removed by water rinsing.

Another object of this invention is to provide a method for a one-step wash for personal care such a hand wash, or equipment wash by employing a highly penetrating germicide foam product.

Another object of this invention is to provide a new and improved combined foam teat dip and teat wash. Specifically, it would be highly desirable to provide a foamed bovine teat dip which would cover the outer teat area, and provide protection to the teat canal when the teat sphincter is open following a milking procedure, when the teat canal is exposed and highly vulnerable to immediate infection. Even when the teat sphincter has closed, it would still be desireable to prevent infection from reaching the area of the teat opening, and the teat area in general with reduced run off. This would enable the foam to adhere to and remain in close and protective contact with the teat. Further, it is desired to provide an apparatus with the capability of producing foam using a wide variety of surfactants, such as those disclosed, supra.

U.S. Pat. Nos. 3,713,423 and 4,305,346 describe an apparatus which coats a bovine teat area with fine spray or mist, but these patented devices are hand operated and do not produce any foam, let alone a foam fulfilling the above protective characteristics. It will also be appreciated that use of foam reduces the amount of surfactant used for a bovine teat dip by about one-half compared to either a spray or liquid dip, and hence an improvement in the operation of these two patents would be desirable.

THE INVENTION

According to the invention, there is provided a method for producing a penetrating germicide foam with inherent lubricating properties to enable washing without pre-wetting, the foam being removable simply by rinsing.

Additionally, according to the invention, there is provided a method for producing a combined foam teat dip and teat wash by pressurizing air with surfactant at a relatively high pressure followed by depressurization of the surfactant at atmospheric pressure to produce a foam which penetrates adherent dirt which can then be readily removed by cloths typically used by dairymen.

The method for producing a foam for a combined teat dip and after-milking teat wash comprises pressurizing a surfactant in a container with air, feeding the compressed air and surfactant to a flow or line mixer, and expanding the mixture of air and surfactant from an initial pressurized value, in the flow or line mixer through an open orifice and down to atmospheric pressure into a container cup surrounding the teat and adjacent udder area. A new and improved surfactant foam, or a mixture of surfactant and biocide is formed thereby which adheres to the teat, with reduced run off.

The foam of this invention is produced with a surfactant alone, or a mixture of surfactant and germicide, bactericide, surfactant, soap or detergent and sufficient, water, and pressuring the mixture with air ($CO_2$, nitrogen, propellant, etc.) to produce a lubricating, penetrating foam which may be used directly as a wash, without pre-wetting, and following washing may be removed by rinsing.

The mixture may be contained in a conventional hand sized container fitted with a hand pump for pressuring the mixture with air ($CO_2$, $N_2$, propellant, etc.) to produce a suitable foam having inherent lubricating properties. This foam may then be applied directly to a user's hands without requiring a pre-wetting, and which is then removed by conventional rinsing.

If desired, in a larger use or industrial setting, particularly when used to produce a combined foam teat dip and teat wash, the container may be of larger size, and air is combined with the surfactant, or surfactant and mixture of germicide, etc., by pressure controlled air pumps. One type of equipment which may be modified to produce the desired type of foam is described in U.S. Pat. Nos. 3,713,423 and 4,305,346. The equipment described in these two patents employs a flow and mixing line for air and surfactant which is connected to the bottom entry of a teat cup, and a spray nozzle mounted at the entry. This equipment may be modified by removing the spray nozzle, thereby forming an open orifice in the teat cup. This modification enables a mixture of surfactant and air to be pressurized in the flow and mixing line. Upon depressurization to atmospheric at the open orifice, the desired quality of combined foam teat dip and teat wash is produced. This foam may then be used as an initial teat dip and a subsequent post dip. Typical flow and mixing line pressures vary between 20–50 psi., and typical flow and mixing line lengths useful in milking operations are about 20–30 feet.

The foam produced by the method of this invention is unique in terms of functioning as a combined bovine teat dip and after-milking teat wash since it adheres to the teat and udder area without significant run off, and forms a bead at the end of the teat. This area of the teat is at significant risk of infection both prior to, and subsequent to milking, and the presence of the bead considerably reduces the possibility of infection. Also, since there is little foam run off, a longer period of protection is afforded against bacterial infection. Moreover, following cessation of milking, use of a post-dip which is not wiped off, enables fresh available liquid and foam to cover the teat end, and enables the open teat sphincter to be covered by the foam bead, when the open sphincter, and hence the teat canal is at high risk of infection.

The method for producing the foam, and the foam produced thereby is also particularly useful for food handlers, such as butchers, food servers and workers directly involved in handling raw, perishable foods which may become laden with bacteria if these foods are left too long without refrigeration. Under these conditions, it would obviously improve the quality of sanitary conditions if a food handler did not splatter food particles, or otherwise directly contact and contaminate a food washing area, or use wiping towels, etc. Instead, if the food handler were to apply the foam product of this invention to their hands, without immediately contacting surrounding areas with contaminated food particles, this would considerably reduce the amount of potential sources of bacteria.

In addition to those surfactants described in the McCutcheon's publications, typical surfactants which may be useful in the foams of this invention are described in U.S. Pat. Nos. 2,977,315; 3,950,544; 4,049,830; 4,258,056; 4,371,517; 4,671,958; 4,678,668; 4,940,702; 5,028,427; 5,175,160; 5,208,257; 5,466,959 (PVP); U.S. Pat. No. 5,529,770 ($C_{16-18}$ fatty alcohols); U.S. Pat. No. 5,616,348 (polyethoxylated polyoxypropylene block copolymer—POLOXAMER); and, German Patent 2,936,934 and incorporated by reference, herein. However, producers, distributors and users of nonyl phenoxy surfactants should be continually aware of ongoing regulations governing the use of specific surfactants in this category when used for bovine teat dips due to possible mutagenic effects of a given surfactant.

Also, surfactants such as polyethenoxy detergents and $I_2$ are disclosed in an article by Benjamin Carroll in the Journal of Bacteriology, 69: 413–417, (1955) may be used in the foams of this invention.

Commercial surfactants containing iodine which are known for use as teat dip formulations include 9–12 mole ethoxylated phenols. A surfactant of this type is sold by Norman Fox & Co. under the trade name of NORFOX N-P9, and listed in "McCutcheon's Emulsifiers and Detergents", (1989 and 1994) specifically for use with iodophors. Another type of teat dip is sold by Klenzade™ Teat Guard, and contains a nonyl phenoxypolyethoxy ethanol surfactant having 1% titratable iodine. Both of these surfactants may also be used in the foam product of this invention, provided they comply with existing regulations.

Applicant's patent, supra, describes a non-ionic, fatty alcohol polyglycol ether carboxylic acid and sold under the trade names of AKYPO™RLM-45, AKYPO™RLM-100, AKYPO™RLM-160, and mixtures thereof, the preferred composition being AKYPO™RLM-100 (Chemical Abstracts Registry 74349-89-6).

Patents which relate either directly or indirectly to foam or defoamers in connection with bovine teat dips are disclosed in U.S. Pat. Nos. 2,989,434; 4,945,110; 5,063,249; 5,370,815; 5,575,993; 5,722,350; 5,843,912; and, 5,967,202. European Patent 077,2973; and, French Patent 2,633,308 also contain bovine teat dip foams.

Germicides or bactericides which may be employed in the foams of this invention include: chlorhexidine, $I_2$, iodides such as $I^-$, HI, or equivalent (e.g., KI, NaI, $CaI_2$, etc.), iodophors, etc., chlorine dioxide, quaternary ammonium compounds, etc. It is well known that when antibiotics, etc., are employed for hand and skin care washes, there is a build-up in resistance by bacteria, and hence it would be preferred to use the least amount of germicide, etc. in these formulations.

The amount of water employed in the foam commercial soap compositions of this invention is typically about 85%–97.5% by weight, and this enables a sufficient dilution of the germicide in the foam to minimize the amount required and satisfy USDA and FDA requirements for the content of sanitizers in commercial soaps, due inter alia to the penetrating capabilities of the foam.

Typical commercial usage for the ready-to-use foams of this invention include institutions such as hospitals and other health care facilities, schools, hotels, public rest rooms, restaurants, food processing plants such as canning facilities, and of course use in the home.

What is claimed is:

1. A method for producing a combined foam teat and udder dip, and after milking post teat dip and udder wash formed by admixing a surfactant with air under pressure in a flow and line mixer and subsequently depressurizing the admixture from an initial pressurized value in the flow and line mixer down to atmospheric pressure, and into an open orifice in a connected teat cup surrounding the teat and adjacent udder area, the consistency of the foam being sufficient to apply penetrating and adherent foam to the teat and surrounding udder area for an effective contact time prior to milking, and without significant run-off, thereby enabling ready removal of deleterious material therefrom; and if desired, following cessation of milking, the post teat dip and after milking and udder wash which is not wiped off enables the foam to adhere to the teat, including the teat end, for a sufficient length of contact time, thereby causing fresh available liquid and foam to cover the teat end, and hence the teat canal opening with foam when the teat sphincter muscle is both open and closed, and thereby reduce the possibility of infection through the teat canal.

2. The method of claim 1, in which the flow and mixing line pressures are at least 20 psi.

3. The method of claim 1, in which the flow and mixing line pressures vary up to 50 psi.

4. The method of claim 1, in which the flow and mixing line lengths are at least 20 feet.

5. The method of claim 1, in which the flow and mixing line lengths vary up to 30 feet.

6. The method of claim 1, in which the flow and mixing line pressures are at least 20 psi and up to 50 psi.

7. The method of claim 1, in which the flow and mixing line lengths are at least 20 feet and up to 30 feet.

8. The method of claim 1, in which the flow and mixing line pressures are at least 20 psi and up to 50 psi and the flow and mixing line lengths are at least 20 feet and up to 30 feet.

* * * * *